US012539394B2

(12) United States Patent
San

(10) Patent No.: US 12,539,394 B2
(45) **Date of Patent: *Feb. 3, 2026**

(54) LIQUID EMBOLIC DELIVERY DEVICE

(71) Applicant: MicroVention, Inc., Aliso Viejo, CA (US)

(72) Inventor: Frida San, Long Beach, CA (US)

(73) Assignee: MICROVENTION, INC., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/326,237

(22) Filed: May 31, 2023

(65) Prior Publication Data

US 2023/0310803 A1 Oct. 5, 2023

Related U.S. Application Data

(63) Continuation of application No. 16/684,359, filed on Nov. 14, 2019, now Pat. No. 11,701,490.

(60) Provisional application No. 62/768,813, filed on Nov. 16, 2018.

(51) Int. Cl.
*A61M 25/01* (2006.01)
*A61M 25/09* (2006.01)

(52) U.S. Cl.
CPC ... *A61M 25/01* (2013.01); *A61M 2025/09008* (2013.01); *A61M 2025/091* (2013.01); *A61M 2025/09183* (2013.01)

(58) Field of Classification Search
CPC ........ A61M 25/01; A61M 2025/09008; A61M 2025/091; A61M 2025/09183; A61M 2025/0006; A61M 25/0075; A61B 2017/1205; A61B 17/12186
See application file for complete search history.

(56) References Cited

U.S. PATENT DOCUMENTS

| | | | | |
|---|---|---|---|---|
| 3,885,710 | A * | 5/1975 | Cohen | A61M 3/005 222/129 |
| 6,139,520 | A | 10/2000 | McCrory et al. | |
| 6,146,373 | A * | 11/2000 | Cragg | A61B 17/12186 604/48 |
| 6,558,367 | B1 | 5/2003 | Cragg et al. | |
| 9,114,215 | B2 * | 8/2015 | Cowan | A61M 5/007 |
| 2007/0003489 | A1 * | 1/2007 | Wright | A61K 9/122 424/47 |
| 2009/0247985 | A1 * | 10/2009 | Melsheimer | A61J 1/2096 604/506 |
| 2010/0114017 | A1 * | 5/2010 | Lenker | A61B 17/221 606/200 |
| 2012/0116351 | A1 | 5/2012 | Chomas et al. | |
| 2012/0172680 | A1 | 7/2012 | Gelfand et al. | |
| 2014/0039459 | A1 * | 2/2014 | Folk | A61B 17/12186 604/509 |

(Continued)

*Primary Examiner* — James M Kish
*Assistant Examiner* — Natasha Patel
(74) *Attorney, Agent, or Firm* — Procopio, Cory, Hargreaves & Savitch LLP

(57) ABSTRACT

Described herein is a liquid embolic delivery device designed to minimize excess embolic solvent buildup therein. The liquid embolic delivery device generally comprises an outer catheter, an inner catheter that is longitudinally moveable within the outer catheter. The inner catheter is used for an initial embolic solvent flush and to deliver liquid embolic, while the outer catheter is used to remove excess solvent.

20 Claims, 6 Drawing Sheets

(56) References Cited

U.S. PATENT DOCUMENTS

2014/0107251 A1 4/2014 Cruise et al.

* cited by examiner

LIQUID EMBOLIC DELIVERY DEVICE

RELATED APPLICATIONS

This application is a continuation of and claims priority to U.S. patent application Ser. No. 16/684,359 filed Nov. 14, 2019 entitled Liquid Embolic Delivery Device, which claims benefit of and priority to U.S. Provisional Application Ser. No. 62/768,813 filed Nov. 16, 2018 entitled Delivery Device, both of which are hereby incorporated herein by reference in their entireties.

BACKGROUND OF THE INVENTION

Liquid embolic agents refer to materials that are delivered within a patient in liquid form and then rapidly embolize or polymerize after delivery. These materials can be helpful in embolizing areas with numerous and/or complex vessels, such as arteriovenous malformations (AVMs). Example liquid embolic agents can be found in U.S. Pat. No. 9,078,950, the contents of which are hereby incorporated by reference.

Typically, a delivery catheter is initially flushed with an embolic solvent to prevent embolization within the catheter's delivery passage, and then the liquid embolic is pushed into the delivery passage and out into the patient. There, the liquid embolic quickly embolizes or polymerizes into a hardened form to block up the vessels.

Liquid embolic agents can be challenging to deliver due to their tendency to embolize quickly, which can result in the liquid embolic agents solidifying and sticking to the interior passage of the delivery catheter. In order to help prevent this solidification within the catheter, the catheter 12 is initially flushed with liquid embolic solvent 20, as seen in FIG. 1, that delays the polymerization process from initiating. Turning to FIG. 2, the liquid embolic agent 22 is then injected into the catheter 12. While this technique may help prevent premature polymerization, the liquid embolic solvent 20 may mix with the initial portion of the liquid embolic agent 22, either within the catheter 12 or outside of the catheter 12 in the vessel 10, causing it to dilute. Additionally, this initial solvent flush step can cause excess embolic solvent 20 to build up in the distal region of the catheter. This excess solvent will eventually make its way into a patient, which can cause complications for patients with DMSO sensitivity.

Often, the liquid embolic agent 22 itself is formed as a specific ratio of copolymer (or similar material) and liquid embolic solvent 20 (e.g., an organic solvent such as DMSO). Hence, when more liquid embolic solvent 20 is mixed in with the pre-mixed liquid embolic agent 22, the ratio of copolymer-to-solvent becomes higher. This dilution of the copolymer can degrade the performance of the liquid embolic agent 22, reducing the speed of polymerization and the amount of material that ultimately polymerizes.

Hence, what is needed is an improved delivery device and technique that reduces this dilution of liquid embolic delivery agent during a procedure.

SUMMARY OF THE INVENTION

The present invention is generally directed to a liquid embolic delivery device, and method of using the same, that reduces dilution of the liquid embolic agent.

In one embodiment, the present invention is directed to a liquid embolic delivery device having an outer catheter and an inner catheter that is longitudinally movable within the outer catheter. Initially, the distal tip of the inner catheter is positioned within the passage of the outer catheter. A valve also seals the distal tip of the outer catheter.

A physician flushes the delivery device by injecting liquid embolic solvent 20 into the inner catheter, which fills the interior passage of the inner catheter and then moves out into the passage of the outer catheter. Next, a vacuum source is applied to the passage of the outer catheter to withdraw the excess liquid embolic solvent 20 from the distal end of the catheter. The liquid embolic agent 22 is then introduced. In one embodiment, a liquid embolic agent 22 is delivered into the interior passage of the inner catheter simultaneous with the withdrawal of the solvent.

Finally, the inner catheter is distally pushed out through the valve at the distal end of the outer catheter. Additional liquid embolic agent is injected into the interior passage of the inner catheter which causes it to be delivered out through the end of the inner catheter.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
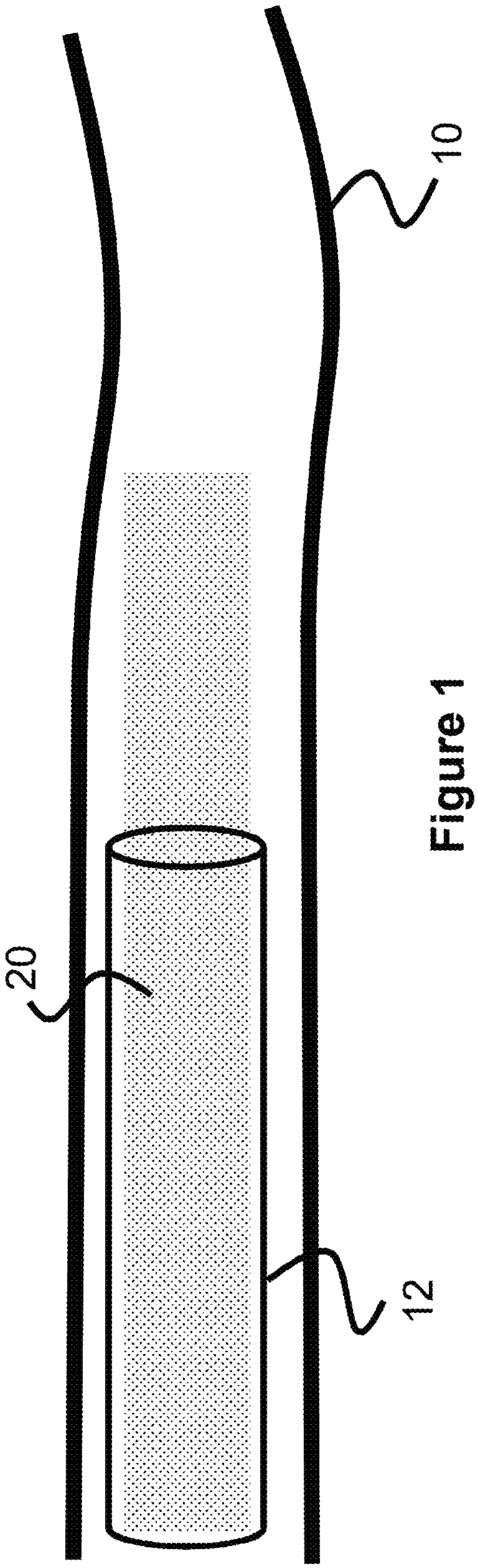
FIG. 1 illustrates a catheter being primed with liquid embolic solvent.
Figure 2:
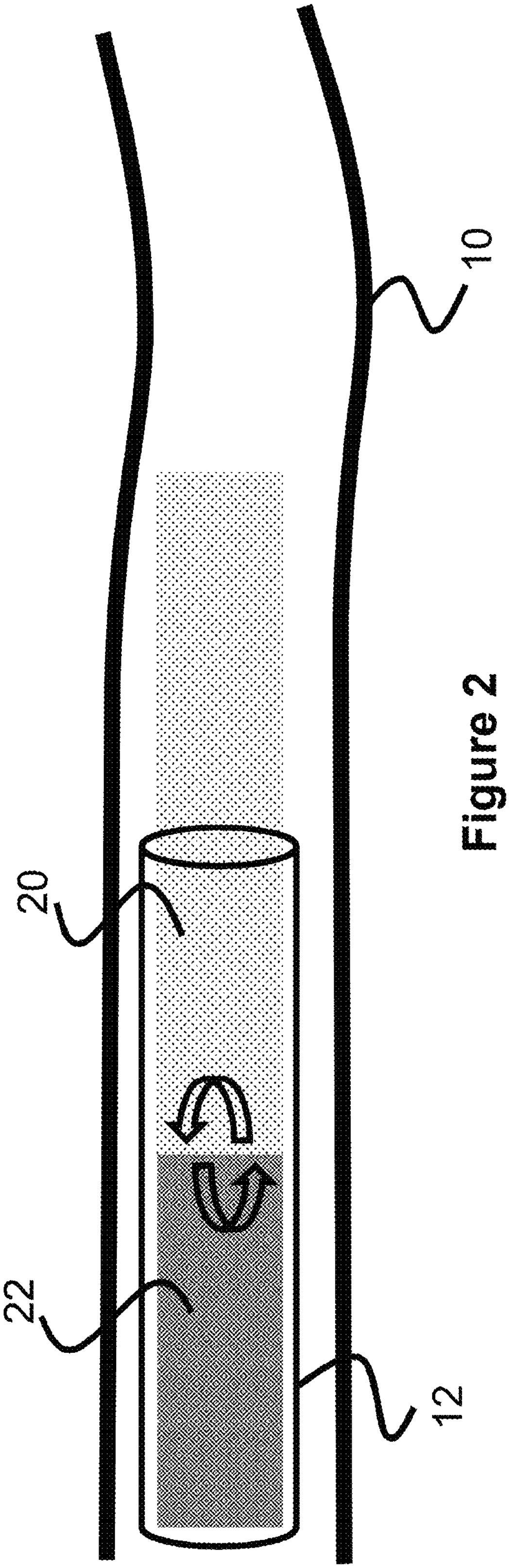
FIG. 2 illustrates a catheter delivering liquid embolic agent that is mixing with excess liquid embolic solvent.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Figure 3:
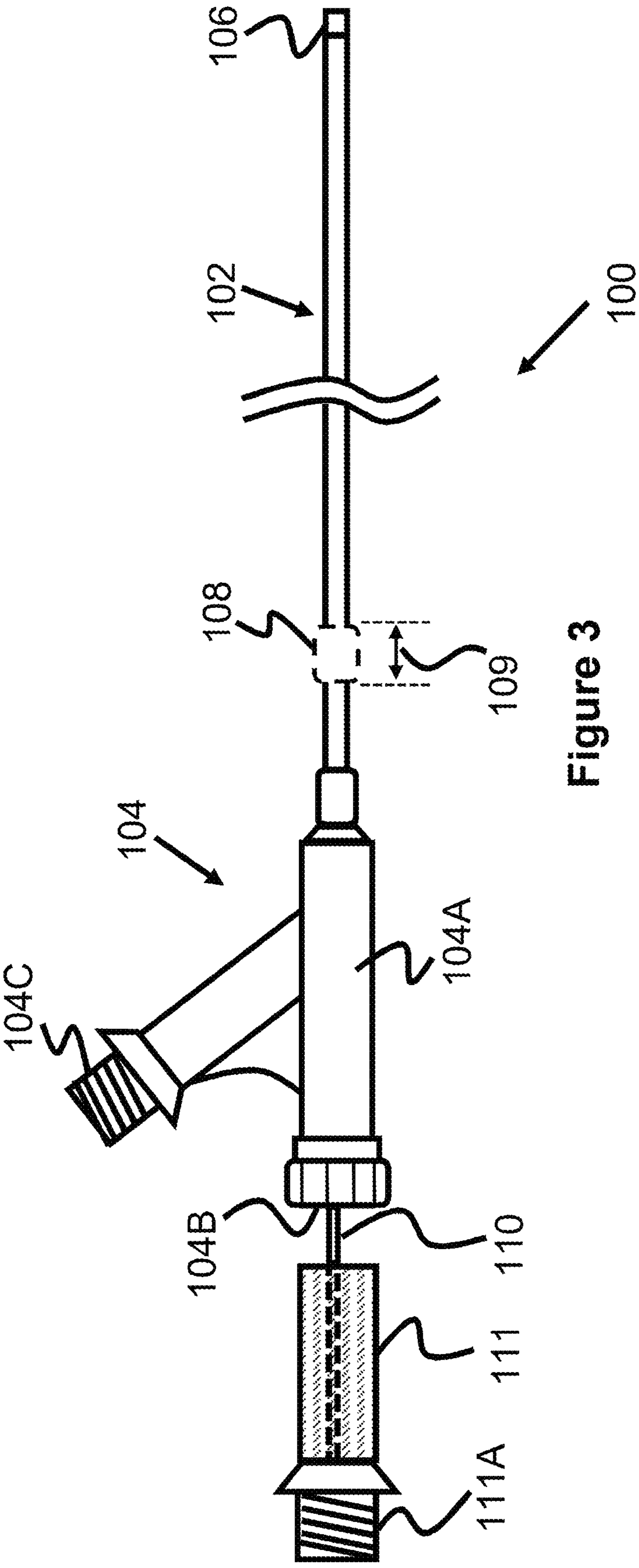
FIG. 3 illustrates a liquid embolic delivery catheter having dual lumens according to the present invention.

FIG. 3 illustrates a liquid embolic delivery device 100 that can be used to minimize or prevent dilution of a liquid embolic agent 22 during a procedure. As previously discussed, when a liquid embolic delivery device is initially flushed with liquid embolic solvent 20, residual solvent 20 remains in the catheter's delivery passage and just outside of the distal tip in the patient's vessel. When the liquid embolic agent 22 is introduced, it mixes with the residual solvent 20, causing the embolic agent to become diluted. This reduces or degrades the performance of the liquid embolic agent 22 when delivered within the patient's vessels. The residual solvent 20 will also eventually make its way into the patient, creating complications for DMSO-sensitive patients.

Generally, in the embodiments of the present invention, this dilution is minimized or eliminated by providing a mechanism to remove most or all of the liquid embolic solvent 20 prior to delivery of the liquid embolic agent 22. In the example embodiment in FIG. 3, this is achieved by including an inner catheter 110 that is longitudinally movable between a first position, sealed within an outer catheter 102, and a second position where a distal end is positioned distally outside of the outer catheter 102. As discussed in greater detail below, liquid embolic solvent 20 is flushed through the inner catheter 110 and into the outer catheter 102. The solvent 20 is then vacuumed/suctioned out of at least the outer catheter 102 and/or the inner catheter 110. The embolic agent 22 is then introduced into the inner catheter 110. In one embodiment, the liquid embolic agent 22 is delivered into the inner catheter 110 simultaneously with the vacuum/suction of the solvent. Finally, the inner catheter 110 is advanced out of the distal end 106 of the outer catheter 102 and additional liquid embolic agent 22 is injected into the inner catheter 110, causing it to advance out of the inner catheter 110 without dilution.

Figure 4:
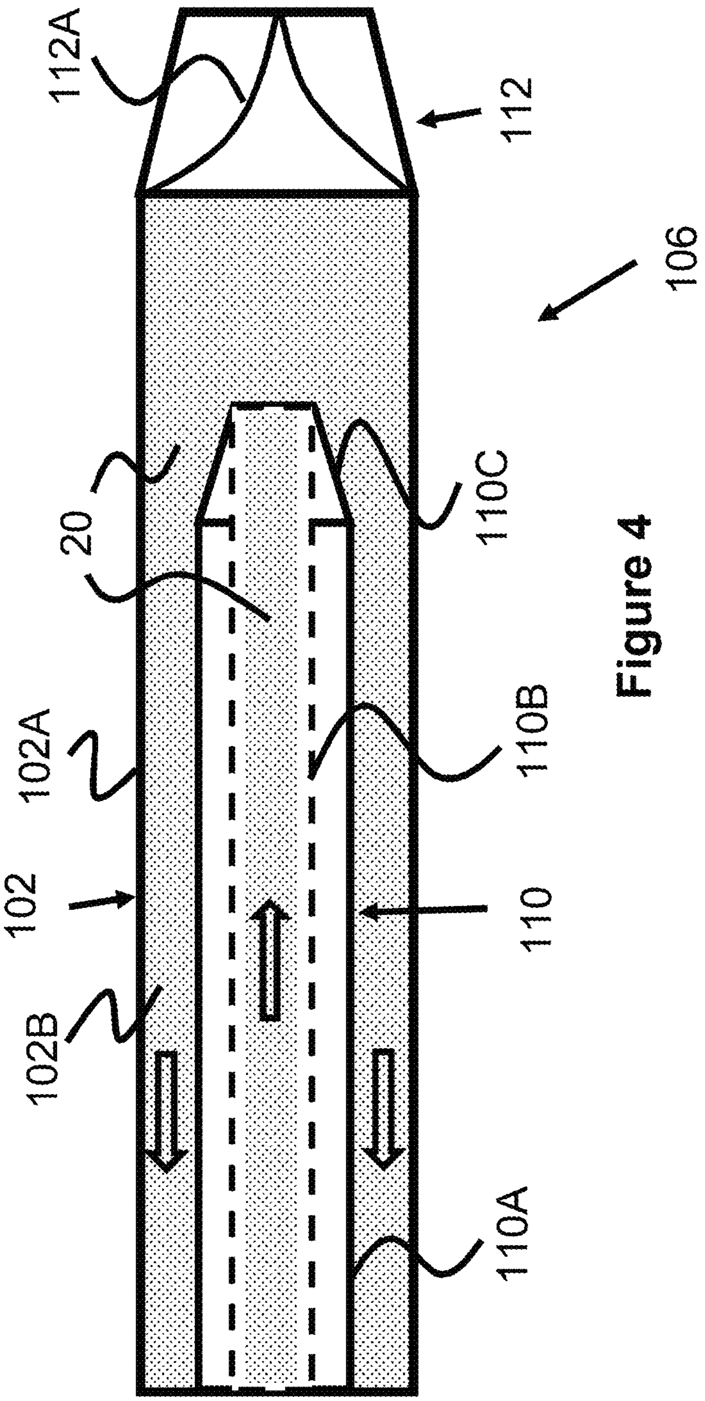
FIG. 4 illustrates a magnified view of the distal end of the liquid embolic delivery catheter of FIG. 3 during a flushing procedure according to the present invention.
Figure 5:
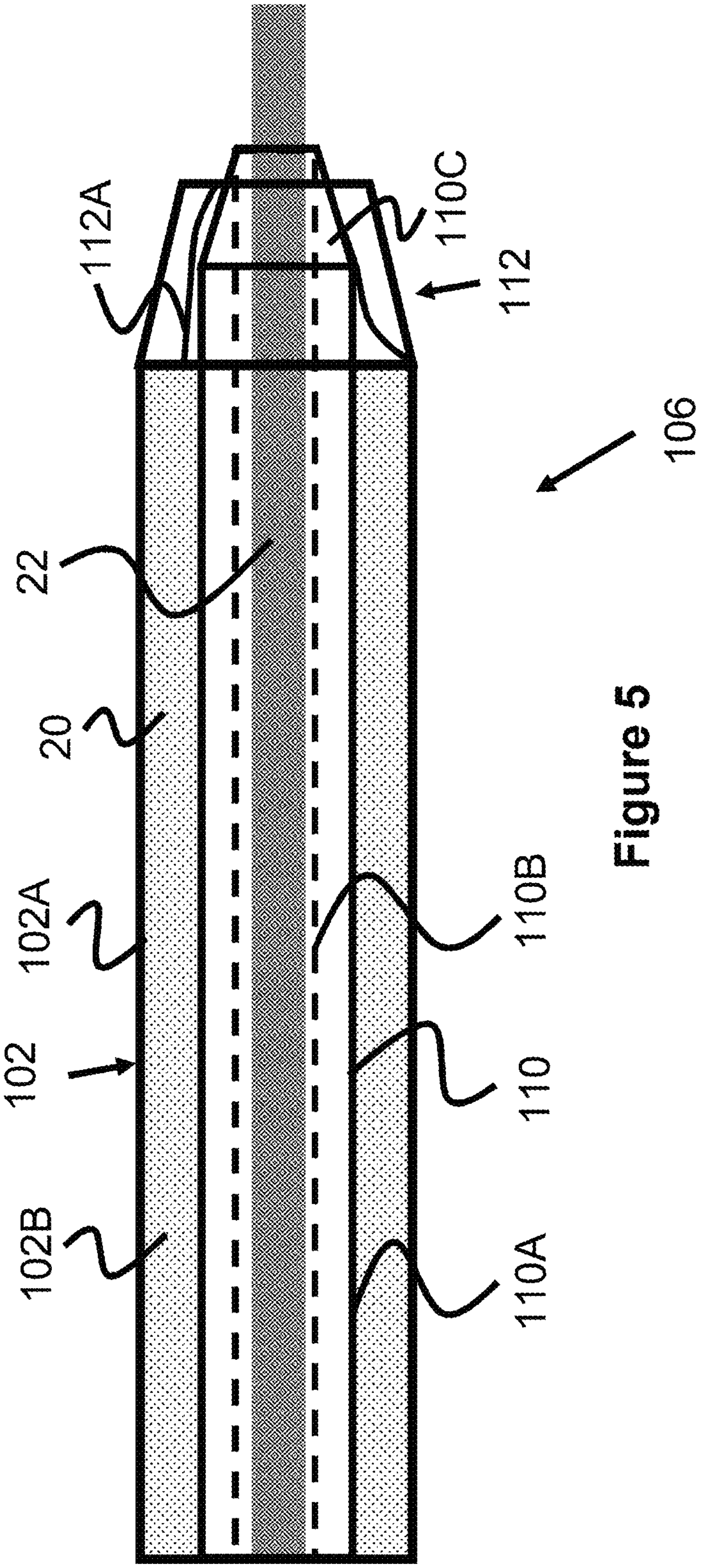
FIG. 5 illustrates a magnified view of the distal end of the liquid embolic delivery catheter of FIG. 3 during delivery of a liquid embolic agent according to the present invention.

Turning first to the outer catheter 102, this comprises a tubular body 102A having a passage 102B extending between its proximal and distal ends, as seen in FIGS. 3 and 4. The distal end of the tubular body 102A is connected to a one-way valve 112 that seals off the passage 102B until pressed or pushed on by the distal tip 110C of the inner catheter 110. In one embodiment, this valve 112 is a duck-billed valve with two or more valve flaps 112A that are angled toward each other in the distal direction. Other valve types are possible, as discussed later with regard to FIG. 6.

The proximal end of the tubular body 102 is connected to a catheter hub 104 that has an elongated, straight body portion 104A that terminates with a main connection aperture 104B having a Tuohy-Borst connection configured to clamp onto the inner catheter 110. A secondary passage splits off from the straight body portion 104A at an angle, terminating with connection aperture 104C having a Luer connection. Both connection apertures 104B and 104C connect to a common internal passage within the hub 104 and therefore are also in communication with the tubular body 102A.

As seen best in FIGS. 3 and 4, the inner catheter 110 is positioned within the first aperture 104B, through the passage of the hub 104, and through the passage 102B of the tubular body 102A. The proximal end of the inner catheter 110 can be coupled to a second hub 111 that allows for connection to different liquid sources that are to be injected into the device 100 via the Luer connection at aperture 111A (e.g., solvent 20 and agent 22).

The inner catheter 110 is preferably composed of an elongated tubular body 110A that forms an inner passage 110B that opens at its distal tip 110C. The distal tip 110C can be beveled or conical to assist in passing through the valve 112 after the device 100 has been flushed. The inner catheter 110 is also at least partially, longitudinally movable within the passage 102B of the tubular body 102A. This allows the user to maintain the distal tip 110C within the passage 102B of the outer catheter 102 and later distally advance the distal tip 110C outside of the outer catheter 102.

FIG. 4 illustrates a magnified view of the distal end 106 of the outer catheter 102 during the preliminary flushing procedure, which precedes delivery of the liquid embolic agent 22. Initially, the distal tip 110C of the inner catheter is positioned within the passage 1028 of the outer catheter 102, proximal of the distal valve 112. The second hub 111 on the inner catheter 110 is connected to a source of liquid embolic solvent 20 (e.g., a syringe) which is injected into the aperture 111A and passage of the second hub 111, passing into the passage 1108 of the inner catheter body 110A. Since the distal tip 110C is positioned proximally of the closed one-way valve 112A, the solvent 20 exits the inner catheter 110 and passes into the passage 1028 of the outer catheter body 102A. Again, the one-way valve 112 is in a closed position so as to retain the solvent 20 within the outer catheter 102.

Next, a source of the liquid embolic agent 22, such as a syringe, is attached to the connection aperture 111A on the second hub 111. The excess solvent 20 is withdrawn from the inner catheter 110 and the liquid embolic agent is introduced into the inner catheter. In one embodiment, the liquid embolic agent 22 is delivered into the inner catheter 110 simultaneously with the withdrawal of the solvent. A vacuum source, such as a syringe, can be attached to the connection aperture 104C of the split-off portion of the hub 104. Again, this aperture 104C is in communication with the passage within the hub 104 and the passage 1028 within the tubular body 102A of the outer catheter 102. In one embodiment, suction is then applied by the vacuum source as a portion of the liquid embolic agent 22 is simultaneously injected into the passage 1108 of the inner catheter 110. This results in the excess solvent 20 being withdrawn from passage 1108 of the inner catheter 110 and into the passage 1028 of the outer catheter 102. At the same time, the liquid embolic agent 22 fills the entire passage 1108, replacing the solvent 20.

In one embodiment, the vacuum source is configured to withdraw all of the excess solvent 20 from the inner catheter 110, leaving the solvent 20 mostly in the outer catheter 102. In another embodiment, the vacuum source may be configured to further remove most of the excess solvent 20 from the outer catheter 102 but leave some near the proximal end of the passage 1028.

In another embodiment, the tubular body 102A includes a balloon 108 (see FIG. 3) near its proximal end that is connected to the passage 1028. As the vacuum source is activated, it pulls the solvent 20 proximally, which fills up the balloon 108. In this respect, the balloon 108 provides extra storage space for the withdrawn solvent 20. In one embodiment, the balloon 108 is disposed over a gap 109 created between two separate segments of the outer tubular body 102A. Each end of the balloon 108 can be fixed to an outer surface of the outer tubular body 102A and can be composed of a relatively stiff balloon material that provides some structural support to the outer catheter 102. The balloon 108 can be positioned at a proximal location of the outer catheter 102 such that it remains outside of the patient during a procedure and thereby avoids potential damage from being advanced through an introducer sheath. Since the gap 109 extends entirely around the circumference of the outer tubular member 102, at least some of the solvent 20 is pulled into the balloon 108 when the vacuum source is applied, allowing for increased storage space for the solvent 20.

In an alternate embodiment, the outer tubular body 102A may have one or more apertures instead of the gap 109. The balloon 108 is fixed over the apertures and functions in a similar manner to the prior embodiment having the gap 109.

Once the solvent 20 has been withdrawn and the inner catheter 110 filled with liquid embolic agent 22, the inner catheter 110 is advanced distally so that the distal tip 110C presses against the valve flaps 112A and the distal tip 110C at least partially passes out of the valve 112. At this point, additional liquid embolic agent 22 is injected into the passage 1108 of the inner catheter 110 which causes the liquid embolic agent 22 to pass through passage 1106, and exit the distal tip 110C into the patient.

Figure 6:
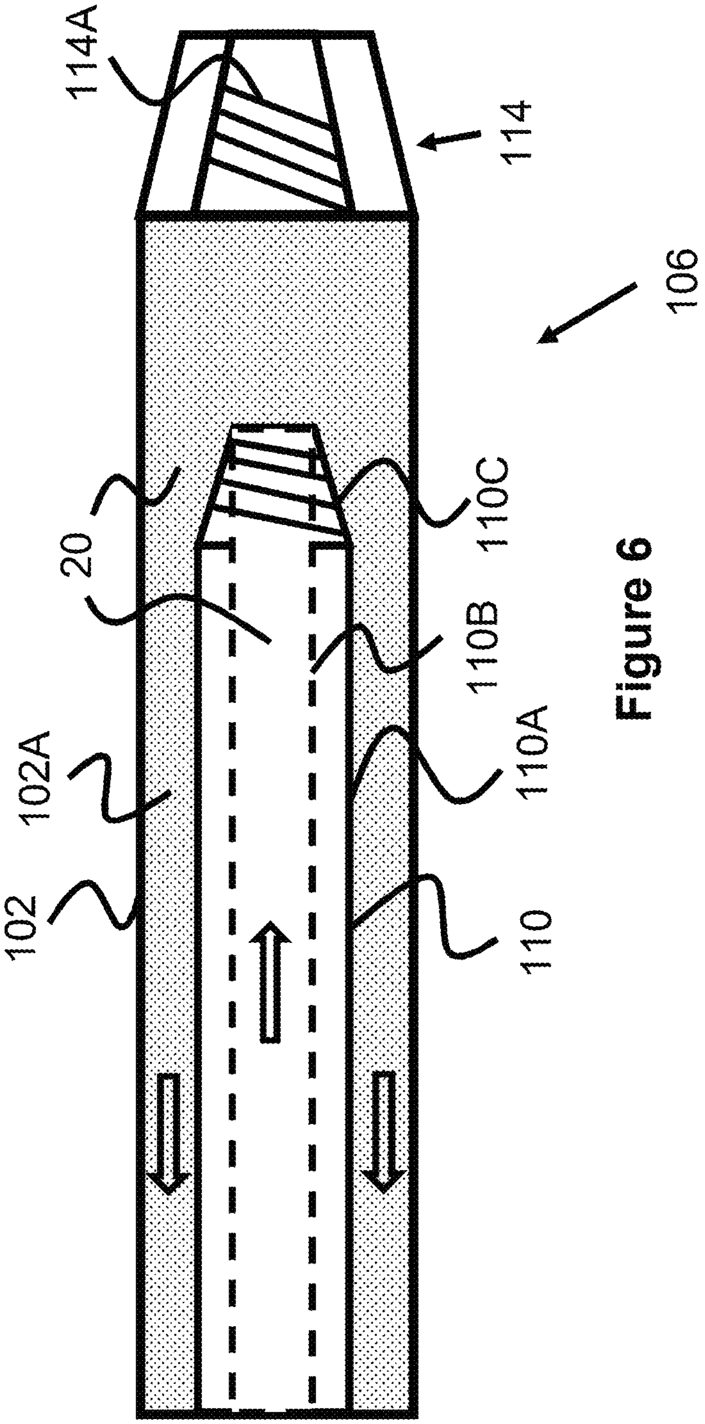
FIG. 6 illustrates a magnified view of a distal end of an alternative liquid embolic delivery catheter according to the present invention.

FIG. 6 illustrates an alternative embodiment that is similar to the previous embodiment except that, instead of a one-way valve opened by pressing the inner catheter 110 through it, the outer catheter 102 has a Luer lock valve mechanism 114 that can engage with the distal tip 110C of the inner catheter 110. Normally, the Luer lock valve 114 is closed, however, when threads on the distal tip 110C are used to screw it into threads 114A on the inner surface of the luer lock 114, it presses open valve flaps (similar to the previous valve 112) within the Luer lock 114, allowing it to open. This opens the inner passage 110B to the outside of the device 100 to allow delivery of the liquid embolic agent 22.

While the prior-discussed embodiments include the use of a vacuum or suction force to assist in the removal of the solvent 20 from the passage 110B of the inner catheter 110, an alternate embodiment is also contemplated that does not use any vacuum or suction force to assist in the removal of the solvent 20. This alternate embodiment is similar to the prior-discussed embodiments but may not necessarily include a suction device such as a syringe.

In the prior embodiments, the suction force is generally applied at about the same time as the liquid embolic agent 22 is initially injected into the passage 110B of inner catheter 110. Performing these actions around the same time allows the liquid embolic agent 22 to take up any space created by the solvent 20 leaving the inner catheter 110. Otherwise vacuum space could be formed within the catheter or the suction force could overpower the valve 112, sucking in blood to the outer catheter 102.

By avoiding the use of a suction force, this alternate embodiment instead relies on the force of the liquid embolic agent 22, when injected, to push the solvent 20 out of the passage 110B of the inner catheter 110. The increased volume of solvent within the outer catheter 102 can be accommodated by the balloon 108 that can expand as necessary, or by exiting through aperture 104C on the first hub 104 into a receptacle.

The flushing procedure and delivery of the liquid embodiment agent 22 of the alternate embodiment would be performed as follows. Initially, the distal tip 110C of the inner catheter is positioned within the passage 102B of the outer catheter 102, proximal of the distal valve 112. The second hub 111 on the inner catheter 110 is connected to a source of liquid embolic solvent 20 (e.g., a syringe) which is injected into the aperture 111A and passage of the second hub 111, passing into the passage 110B of the inner catheter body 110A. Since the distal tip 110C is positioned proximally of the closed one-way valve 112A, the solvent 20 exits the inner catheter 110 and passes into the passage 102B of the outer catheter body 102A. Again, the one-way valve 112 is in a closed position so as to retain the solvent 20 within the outer catheter 102.

Next, a source of the liquid embolic agent 22, such as a syringe, is attached to the connection aperture 111A on the second hub 111. The liquid embolic agent is introduced into the inner catheter 110 which causes the solvent 20 within passage 1108 to be pushed out into the passage of the tubular body 102A. The excess solvent 20 that was displaced from the passage 1108 can be accommodated by allowing some solvent 20 to move into and expand the balloon 108, if present on the outer catheter 102. Alternately or additionally, some of the solvent 20 can be pushed out of the aperture 104C and into a receptacle. Alternatively still, the solvent 20 can simply remain in the volume defined by the region between the inner 110 and outer 102 catheter.

Once the solvent 20 has been pushed out of the inner catheter 110 and filled with liquid embolic agent 22, the inner catheter 110 is advanced distally so that the distal tip 110C presses against the valve flaps 112A and the distal tip 110C at least partially passes out of the valve 112. At this point, additional liquid embolic agent 22 is injected into the passage 1108 of the inner catheter 110 which causes the liquid embolic agent 22 to pass through passage 1106, and exit the distal tip 110C into the patient.

In any of the embodiments disclosed in this specification, the solvent 20 can be DMSO and the embolic agent 22 can be a solution of DMSO and a copolymer. Specific examples can be found in U.S. Pat. No. 9,078,950, which was previously incorporated by reference. However, it is contemplated that any type of solvent 20 and liquid embolic agent 22 can be used according to the present invention.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A liquid embolic agent delivery device, comprising:

a first elongated tube having an outer passage and a valve at a distal tip of the first elongated tube, the valve disposed across the outer passage;

a second elongated tube within the first elongated tube and positioned at least partially within the outer passage; and wherein the second elongated tube is interchangeably in fluid communication with a volume of an embolic solvent and a volume of an embolic agent;

wherein the second elongated tube is adjustable between a first configuration and a second configuration, wherein in the first configuration the second elongated tube is positioned proximal of the valve, and wherein in the second configuration a distal tip of the second elongated tube at least partially engages with the valve at the distal tip of the first elongated tube; and wherein in the first configuration, the second elongated tube is in fluid communication with the volume of the embolic solvent, and in the second configuration, the second elongated tube is in fluid communication with the volume of the embolic agent.

2. The liquid embolic agent delivery device of claim 1, wherein the valve is disposed at a distal portion of the first elongated tube.

3. The liquid embolic agent delivery device of claim 1, further comprising a first hub connected at a proximal end of the first elongated tube.

4. The liquid embolic agent delivery device of claim 3, wherein the first hub has at least one aperture, the at least one aperture being connected to a first hub passage in communication with the outer passage.

5. The liquid embolic agent delivery device of claim 3, further comprising a second hub located on a proximal end of the second elongated tube.

6. The liquid embolic agent delivery device of claim 1, wherein the valve is a duck-bill valve.

7. The liquid embolic agent delivery device of claim 1, wherein the valve is a luer lock valve.

8. The liquid embolic agent delivery device of claim 1, further comprising a solvent container.

9. The liquid embolic agent delivery device of claim 8, wherein the solvent container is comprised of a balloon.

10. The liquid embolic agent delivery device of claim 8, further comprising a vacuum source in communication with the first elongated tube.

11. The liquid embolic agent delivery device of claim 10, wherein the solvent container is in fluid communication with the vacuum source such that the embolic solvent is withdrawn into the solvent container when the vacuum source is activated.

12. A liquid delivery device, comprising:

an outer catheter having an outer passage and a valve at a distal tip of the outer catheter, the valve disposed across the outer passage;

an inner catheter within the outer catheter and at least partially within the outer passage;

a first fluid source including a volume of a first fluid; and a second fluid source including a volume of a second fluid;

wherein the first fluid source and the second fluid source are each interchangeably fluidly connected to the inner catheter;

wherein the inner catheter is adjustable between a first configuration and a second configuration, wherein in the first configuration the inner catheter is positioned proximal of the valve, and wherein in the second configuration a distal tip of the inner catheter at least partially engages with the valve at the distal tip of the outer catheter; and wherein in the first configuration, the inner catheter is in fluid communication with the volume of the first fluid, and in the second configuration, the inner catheter is in fluid communication with the volume of the second fluid.

13. The liquid delivery device of claim 12, further comprising a first hub connected at a proximal end of the outer catheter.

14. The liquid delivery device of claim 13, further comprising a second hub located on a proximal end of the inner catheter.

15. The liquid delivery device of claim 13, wherein the first hub includes a common passage connected to a first access aperture and a second access aperture.

16. The liquid delivery device of claim 15, wherein the inner catheter is positioned through the first access aperture of the first hub.

17. The liquid delivery device of claim 16, further comprising a vacuum source connected to the second access aperture.

18. The liquid delivery device of claim 17, further comprising a solvent container, wherein the solvent container is in fluid communication with the vacuum source, wherein the first fluid comprises an embolic solvent and the second fluid comprises an embolic agent, and wherein in an activated configuration the embolic solvent is withdrawn into the solvent container.

19. The liquid delivery device of claim 12, further comprising:

a solvent container; and a vacuum source in fluid communication with the outer catheter, wherein in an activated configuration the vacuum source withdraws the first fluid into the solvent container.

20. A liquid embolic agent delivery device, comprising:

a first delivery means having an outer passage and a valve at a distal tip of the first delivery means, the valve disposed across the outer passage; and a second delivery means within the first delivery means and positioned at least partially within the outer passage;

wherein the second delivery means is interchangeably in fluid communication with a means for supplying an embolic solvent and a means for supplying an embolic agent; and wherein the second delivery means is adjustable between a first configuration and a second configuration, wherein in the first configuration a distal tip of the second delivery means is positioned proximal of the valve, and wherein in the second configuration the second delivery means least partially engages with the valve at the distal tip of the first delivery means; and wherein in the first configuration, the second delivery means is in fluid communication with the embolic solvent, and in the second configuration, the second delivery means is in fluid communication with the embolic agent.

* * * * *